(12) United States Patent
Bade et al.

(10) Patent No.: US 7,950,296 B2
(45) Date of Patent: May 31, 2011

(54) CONTINUOUS FLOW SAMPLE INTRODUCTION APPARATUS AND METHOD

(75) Inventors: Robert K. Bade, Bartlesville, OK (US); Steven H. Trimble, Bartlesville, OK (US)

(73) Assignee: Siemens Industry, Inc., Alpharetta, GA (US)

( * ) Notice: Subject to any disclaimer, the term of this patent is extended or adjusted under 35 U.S.C. 154(b) by 387 days.

(21) Appl. No.: 12/128,941

(22) Filed: May 29, 2008

(65) Prior Publication Data

US 2009/0007624 A1  Jan. 8, 2009

Related U.S. Application Data

(60) Provisional application No. 60/941,304, filed on Jun. 1, 2007.

(51) Int. Cl.
*G01N 1/22* (2006.01)
(52) U.S. Cl. ...................................................... 73/864
(58) Field of Classification Search .................. 73/864, 73/864.21, 864.81
See application file for complete search history.

(56) References Cited

U.S. PATENT DOCUMENTS

| | | | | |
|---|---|---|---|---|
| 3,827,302 A * | 8/1974 | Sato | ............................ | 73/863.33 |
| 4,271,697 A * | 6/1981 | Mowery, Jr. | .................. | 73/61.52 |
| 4,271,703 A | 6/1981 | Roof | ............................ | 73/863.11 |
| 5,492,555 A * | 2/1996 | Strunk et al. | ....................... | 95/86 |
| 6,454,947 B1 | 9/2002 | Safir et al. | ....................... | 506/112 |

FOREIGN PATENT DOCUMENTS

| EP | 0329290 A | 9/1989 |
|---|---|---|
| EP | 0396884 A | 11/1990 |
| EP | 0730151 A | 9/1996 |
| EP | 1243922 A | 9/2002 |
| EP | 1457774 A | 9/2004 |

* cited by examiner

*Primary Examiner* — Hezron Williams
*Assistant Examiner* — Tamiko D Bellamy
(74) *Attorney, Agent, or Firm* — Filip A. Kowalewski

(57) ABSTRACT

The present invention relates generally to an apparatus and method for sample analysis. More particularly, the invention encompasses a method and an apparatus for continuous, constant, flow sample introduction of fluid samples of varying viscosity and composition. The invention further includes the option of the apparatus being associated with at least one fluid analyzer system. A temperature controlled environment may also be provided for the processing and analysis of a fluid sample.

31 Claims, 3 Drawing Sheets

CONTINUOUS FLOW SAMPLE INTRODUCTION APPARATUS AND METHOD

CROSS-REFERENCE TO RELATED APPLICATION

The instant patent application is related to U.S. Provisional Patent Application Ser. No. 60/941,304, filed on Jun. 1, 2007, titled "Technique for Continuous, Constant Flow Sample Introduction," the disclosure of which is incorporated herein by reference.

FIELD OF THE INVENTION

The present invention relates generally to an apparatus and method for sample analysis. More particularly, the invention encompasses a method and an apparatus for continuous, constant, flow sample introduction of fluid samples of varying viscosity and composition. The invention further includes the option of the apparatus being associated with at least one fluid analyzer system. A temperature controlled environment may also be provided for the processing and analysis of a fluid sample.

BACKGROUND INFORMATION

Fluid samples are often introduced to process analyzers with valves that provide a fixed amount of sample. Some process analyzers require a continuous, constant flow of sample. This can be achieved by ensuring that the flow rate of the sample remains constant while it is being introduced and processed by the analyzer. One way to achieve a constant flow rate is by passing a stable viscosity sample through a restrictor at constant pressure. This will not work for a sample whose viscosity is changing unpredictably. Any change in the composition of the fluid sample can result in a change in viscosity, and, hence a subsequent change in its flow rate through the restrictor. The nature of flare samples is that they frequently undergo unpredictable and dramatic compositional changes. This dramatic variation in the composition of the flare lines and the resulting changes in viscosity can make the control of the flow rate of a sample of flare line gas a difficult problem.

Ulrich Gokeler and Friedhelm Müller, in "On Line Monitoring Of Total Sulfur In Combustion Fuel Using Process Gas Chromatography", 2001 ISA Analysis Division Proceedings, Houston, Tex., October 2001, the disclosure of which is incorporated herein by reference, describes an analytical system for an automatic online total sulfur analyzer based on a proven process gas chromatographic technique utilizing a new and unique system to vaporize small amounts of sample continuously. The vaporized sample is continuously burned in a Flame Ionization Detector (FID) flame to produce, various components of the sample, such as, for example, sulfur dioxide, water and carbon dioxide. The sulfur dioxide, represents the entire sulfur content in the sample, which is then separated using conventional gas chromatography and detected utilizing a Flame Photometric Detector (FPD).

U.S. Pat. No. 6,453,725 (Robert W. Dahlgren, et al.), the disclosure of which is incorporated herein by reference, discloses a multi-port, diaphragm sealed valve suitable for use as both a sampling and column switching valve. The valve is constructed to internally block fluid communication between one or more pairs of ports in a valve operating mode. Such blocking may be used to conserve carrier gas when the valve is in the ON position.

Even with these improvements, a need exists for an improved apparatus and method for fluid sample introduction.

Thus, a need exists for a method and an apparatus for a continuous, constant flow, sample introduction for compositionally unstable fluids.

A need also exists for associating at least one fluid analyzer system with an apparatus for a continuous, constant flow, sample introduction.

This invention also overcomes the problems of the prior art. The invention provides a method and an apparatus for an automatically compensating continuous, constant flow, sample introduction system.

PURPOSES AND SUMMARY OF THE INVENTION

The invention is a novel method and an apparatus for a continuous, constant flow sample introduction.

Therefore, one purpose of this invention is to provide a novel method and an apparatus for a continuous, constant flow, sample introduction.

Another purpose of this invention is to provide a method and apparatus where while one sample valve is being filled with a sample fluid at least a second sample valve is sending a sample fluid to be analyzed.

Yet another purpose of this invention is to have the fluid sample processed in a temperature controlled environment.

Still, yet another purpose of this invention is to have a continuous, constant flow of the fluid sample regardless of changes in the viscosity of the sample caused by unpredictable compositional sample changes.

Therefore, one aspect this invention comprises an apparatus for continuous, constant, flow sample introduction, comprising:

(a) at least one sample line having at least one sample fluid;

(b) at least one sampling system for processing said at least one sample fluid;

(c) at least one electronic pressure controller for processing at least one carrier fluid; and (d) at least one first sampling valve and at least one second sampling valve, wherein said first sampling valve is connected to said second sampling valve in series, and wherein said first sampling valve and said second sampling valve are configured such that while said first sampling valve is processing said fluids to be analyzed the second sampling valve is being replenished with fluids to be analyzed, and wherein said fluids to be analyzed comprise said at least one sample fluid and said at least one carrier fluid.

Another aspect this invention comprises a process for continuous, constant, flow sample introduction, comprising:

(a) forwarding at least one sample fluid from at least one sample line to at least one first sampling valve or at least one second sampling valve via at least one sampling system;

(b) forwarding at least one carrier fluid to said at least one first sampling valve or at least one second sampling valve via at least one electronic pressure controller;

(c) processing a fluid to be analyzed in said first sampling valve or said second sampling valve, wherein said fluid to be analyzed comprises said at least one carrier fluid and said at least one sample fluid; and (d) wherein said at least one first sampling valve and at least one second sampling valve are connected in series, and wherein said first sampling valve and said second sampling valve are configured such that while said first sampling valve is processing said fluids to be analyzed the second sampling valve is being replenished with fluids to be analyzed.

BRIEF DESCRIPTION OF THE DRAWINGS

The features of the invention that are novel and the elements characteristic of the invention are set forth with particularity in the appended claims. The drawings are for illustration purposes only and are not drawn to scale. Furthermore, like numbers represent like features in the drawings. The invention itself, both as to organization and method of operation, may best be understood by reference to the detailed description which follows taken in conjunction with the accompanying drawings in which:

DETAILED DESCRIPTION

This invention allows the continuous introduction of a fluid sample to an on-line analyzer at a constant flow rate, even if the viscosity of the sample changes due to changes in the sample's composition. The fluid sample is pushed through the analyzer with a carrier fluid at a constant flow rate. Preferably, at least two valves are used in series to introduce the fluid sample to the flowing stream. The valves are alternately switched so that while one valve is being filled with the sample fluid, the other valve is delivering the sample fluid to at least one fluid sample analyzer. The flow rate is determined by the flow of the carrier fluid which has a constant viscosity. Thus, the viscosity of the fluid sample does not affect the flow of the sample. For purposes of illustration only, an example of how this invention can be used is provided. The example, that is provided, only for the purposes of illustration of this invention, is the measurement of total sulfur in a petrochemical plant flare line. The illustrated example is for a vapor sample, however, it should be understood that the invention can also be used for any fluid sample, such as, for example, a liquid sample.

Figure 1A:
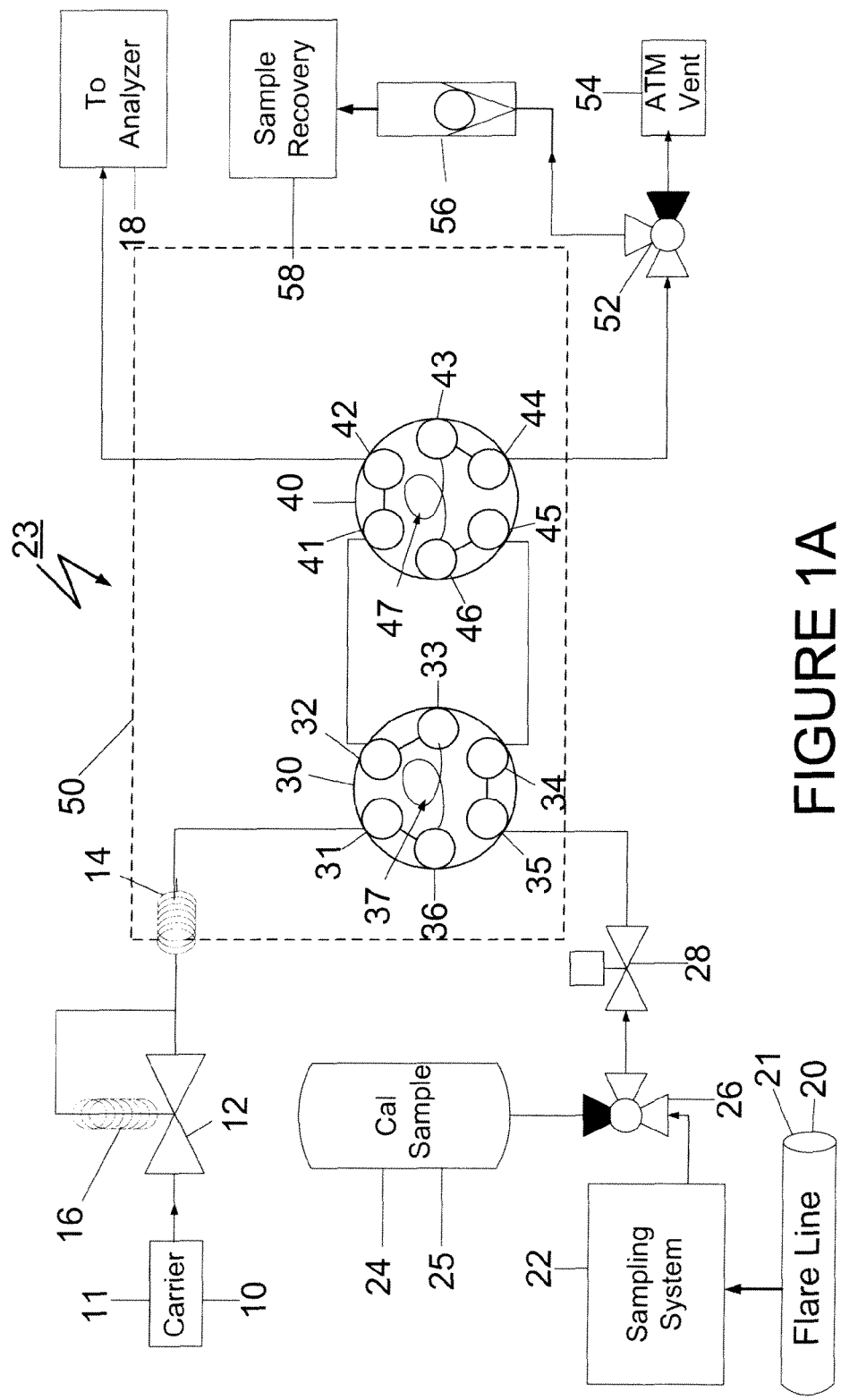
FIG. 1A is an exemplary continuous flow sample introduction apparatus which is used to illustrate a first embodiment of the present invention, in one state of operation.

FIG. 1A is an exemplary continuous flow sample introduction apparatus 23, which is used to illustrate a first embodiment of the present invention, in one or first state of operation.

Figure 1B:
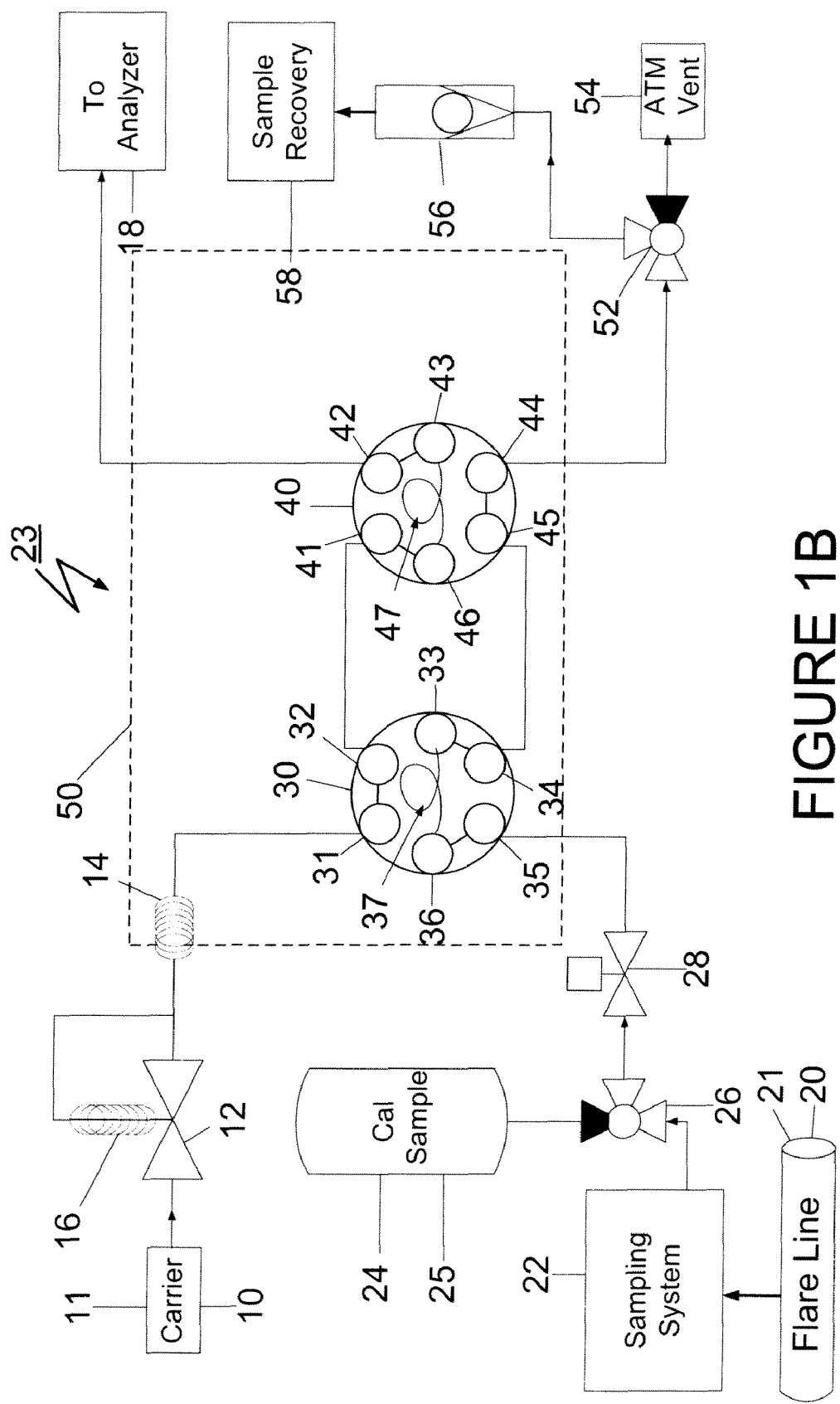
FIG. 1B is an exemplary continuous flow sample introduction apparatus which is used to illustrate a first embodiment of the present invention, in another state of operation.

FIG. 1B is an exemplary continuous flow sample introduction apparatus 23, which is used to illustrate a first embodiment of the present invention, in another or second state of operation.

Referring to FIGS. 1A and 1B, a sample introduction system 23, has at least one sample introduction line 21, having at least one sample to be analyzed 20, or sample 20, such as, for example, a flare line 21, having a flare line sample 20. The sample 20, from the flare line 21, is brought to a normal sampling system 22, for filtration and simple flow control. The sample flow is then sent to two sampling valves, SV1 (Sampling Valve 1) 30, and SV2 (Sampling Valve 2) 40, which are preferably plumbed in series.

SV1 (Sampling Valve 1) 30, is preferably a 6-port valve, comprising ports 31, 32, 33, 34, 35 and 36, and where sample loop 37, connects port 36 with port 33. In an active state port 31 is connected to port 36, port 32 is connected to port 33, and port 34 is connected to port 35, for the flow path, as shown in FIG. 1A. However, in an inactive or relaxed state port 31 is connected to port 32, port 33 is connected to port 34, and port 35 is connected to port 36, for the flow path, as shown in FIG. 1B. It should be appreciated that the sample loop 37, stores the sample to be analyzed 20.

SV2 (Sampling Valve 2) 40, is preferably a 6-port valve, comprising ports 41, 42, 43, 44, 45 and 46, and where sample loop 47, connects port 46 with port 43. In an active state port 41 is connected to port 46, port 42 is connected to port 43, and port 44 is connected to port 45, for the flow path, as shown in FIG. 1B. However, in an inactive or relaxed state port 41 is connected to port 42, port 43 is connected to port 44, and port 45 is connected to port 46, for the flow path, as shown in FIG. 1A. It should be appreciated that the sample loop 47, stores the sample to be analyzed 20.

At least one calibration sample container or unit 25, containing at least one calibration sample fluid 24, is preferably connected to a calibration valve 26, which is an either or valve 26, so that calibration valve 26, either allows the passage of calibration sample 24, or the flare line sample 20, from the sampling system 22.

It is preferred that the calibration sample fluid 24, is a non-interfering fluid 24, or a non-reactive fluid 24. The calibration sample fluid 24, from the calibration sample unit 25, is selected from a group consisting of argon, helium, propane, methane, ethane, nitrogen, or similar fluid, to name a few. Known amounts of one or more compounds of interest or compounds containing one more elements of interest are also present in the calibration sample fluid 24, such as, for example, 500 ppmv carbonyl sulfide in propane.

At least one carrier fluid 10, contained in a container or reservoir 11, such as, a carrier gas 10, for example, helium 10, is also sent to the sampling valves SV1 30, and SV2 40. The flow of the carrier gas 10, is preferably controlled by changing the pressure on a pressure regulator 12, such as, an EPC (Electronic Pressure Controller) 12. The flow of the carrier gas 10, goes to at least one restrictor 14, which is preferably located in a temperature controlled environment 50, such as, an oven 50. The EPC 12, may also have at least one proportional solenoid valve 16, for the management of pressure of carrier gas 10, to the restrictor 14. It is within the realm of a person skilled in the art to replace the EPC 12, the proportional solenoid valve 16, and the restrictor 14, with an electronic flow controller (not shown) or a mechanical flow controller (not shown).

It is preferred that the carrier fluid 10, is a non-interfering fluid 10, or a non-reactive fluid 10. The carrier fluid 10, could be selected from a group consisting of Argon, Helium, Nitrogen, to name a few.

It is preferred that the restrictor 14, is chosen to be of a high flow restriction relative to other restriction in the flow path. This high flow restriction will result in the flow rate of the sample 20, through the sampling valves SV1 30, and SV2 40, to be high relative or compared to the flow of the carrier fluid 10. A flow rate of about 200 mL/min is a preferable flow rate for the flow of sample fluid 20, from the sampling system 22, while, a flow rate of between about 1 to about 2 mL/min is a preferable flow rate for the carrier fluid 10. It is preferred that the flow rate for the sample fluid 20, is between about 150 mL/min to about 250 mL/min, and preferably between about 180 mL/min to about 220 mL/min, and more preferably about 200 mL/min. It is preferred that the flow rate for the carrier fluid 10, is between about 0.50 mL/min to about 2.50 mL/min, and preferably between about 0.80 mL/min to about 2.20 mL/min, and more preferably between about 1.00 mL/min to about 2.00 mL/min.

To initiate the continuous, constant, sampling process any of the sampling valves are actuated. For the purposes of illustration only, sample valve SV1 30, is actuated to change the flow path of carrier fluid 10, to go from port 31, of the valve 30, to port 36, and then push the sample 20, from the sample loop 37, to port 33, and then port 32, and out to port 41, of the SV2 40, as illustrated in FIG. 1A. The sample 20, is then processed through port 42, and is then sent to at least one analyzer system 60, via line 18.

While SV1 30, is processing the sample 20, the flow is being monitored by methods well known in the art. At an appropriate time, before the entire sample 20, in the sample loop 37 has been used SV1 30, is de-actuated and SV2 40, is actuated. The carrier fluid 10, then flows through port 31 to port 32, of SV1 30, and out to port 41 to port 46 of SV2 40, which pushes the sample 20, out of the sample loop 47, to port 43 to port 42, and then out to the analyzer system 60, via line 18, as more clearly illustrated in FIG. 1B. Once again this flow of the carrier fluid 10, is stopped and switched back to the sample loop 37, prior to using up the entire sample 20, in the sample loop 47.

It should be appreciated that while the sample 20, is being delivered from SV1 30, to the analyzer system 60, the sample loop 47, of SV2 40, is being replenished or reloaded with sample 20, from the sample system 22. After the sampling loop 47, is reloaded with the sample 20, the SSO (Sample Shut Off) Valve 28, is actuated which will stop the flow of sample 20, through SV2 40. At least one ARV (Atmospheric Reference Valve) 52, is then actuated which allow the sample pressure to equilibrate with the atmospheric pressure. The ARV 52, is preferably an either or valve 52, so that the sample 20, coming from SV2 40, is either sent to at least one ATM (Atmospheric Management) vent 54, or sent to sample recovery 58, via at least one flow indicator 56.

It should be understood that when SV1 30, is de-actuated and SV2 40, is actuated the ARV 52, and SSO valve 28, are de-actuated for a period of time to allow the sample loop 37, of SV1 30, to be reloaded with the sample 20, from the sample system 22. During this period the SSO (Sample Shut Off) Valve 28, is actuated thus stopping the flow of sample 20, through the SV1 30. The ARV (Atmospheric Reference Valve) 52, is then actuated which allows the sample pressure to equilibrate with the atmospheric pressure. Thus, ARV 52, equilibrates the sample loop 37 and 47, with atmospheric pressure after the replenishment or reloading of the sample 20, from the sample system 22.

As stated earlier that the sample loop 37, and the sample loop 47, are primarily used to store the sample to be analyzed 20, such that, as the sample to be analyzed 20, is being used or exhausted in one sample loop, the other sample loop is actively being reloaded or replenished with the fluid sample to be analyzed 20. It should also be understood that the driving force to move the sample to be analyzed 20, from the sample loop 37 or 47, to an analyzer 60, more clearly discussed with reference to FIG. 2, is the carrier fluid 10.

This process of introducing carrier fluid 10, and sample fluid 20, into SV1 30, and SV2 40, and alternating between SV1 30, and SV2 40, in a repeated manner essentially provides a continuous, constant, flow of sample fluid 20, to the analyzer system 60, at a constant flow rate regardless of sample viscosity or composition. In other words while one sample valve is being filled with the sample fluid 20, the second sample valve is allowing the flow of the sample fluid 20, thus creating the continuous, constant, flow of the sample fluid 20, through the continuous flow sample introduction apparatus 23. It should be understood that the flow rates, sample loop sizes, and timing can be adjusted to accommodate each application.

Figure 2:
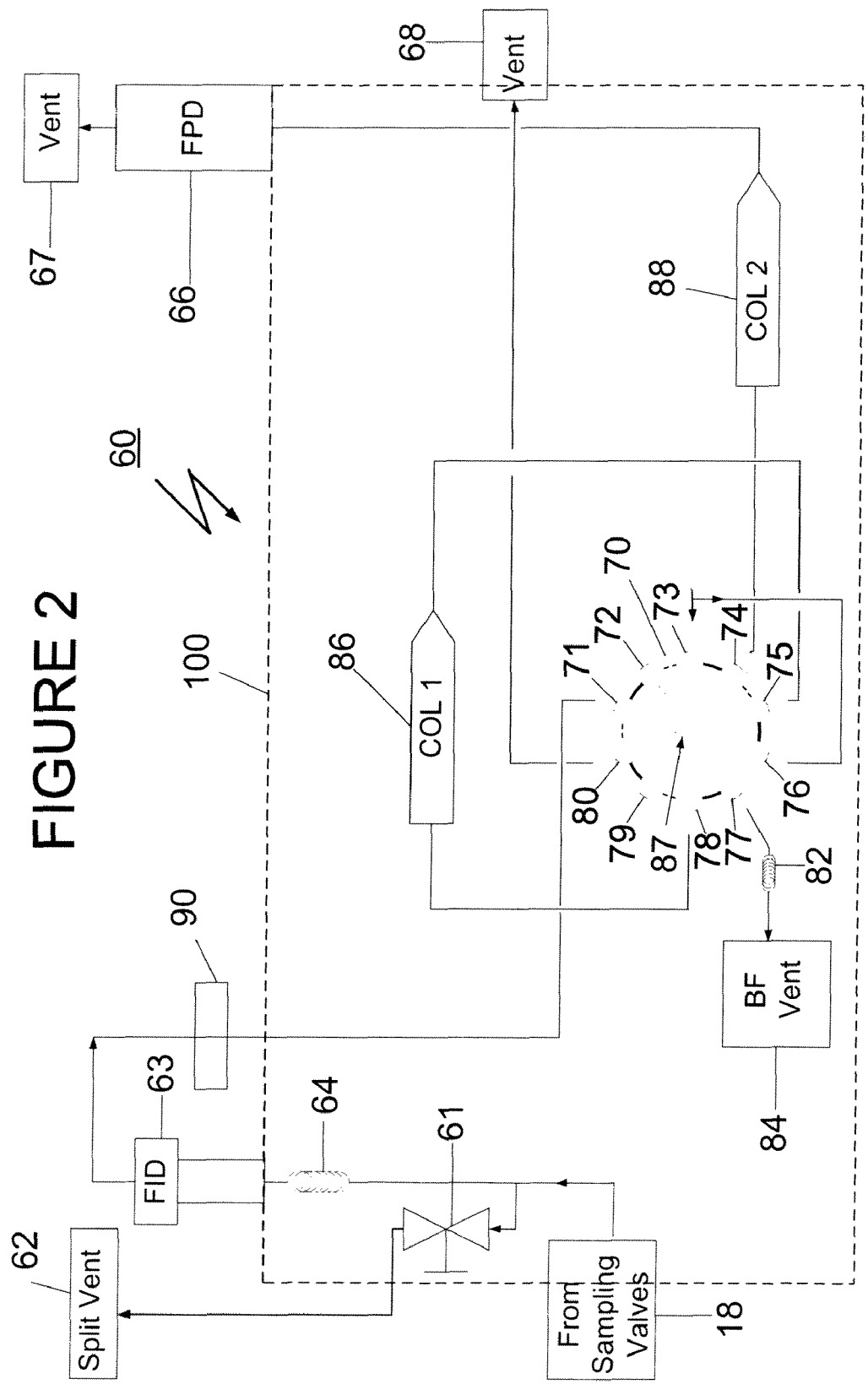
FIG. 2 is an exemplary continuous flow sample introduction apparatus having at least one analyzer system associated therewith and is used to illustrate a second embodiment of the present invention.

FIG. 2 is an exemplary continuous flow sample introduction apparatus 23, having at least one analyzer system 60, associated therewith and is used to illustrate a second embodiment of the present invention. As stated earlier this invention can be associated with a number of different types of analyzers, as it can provide a continuous flow sample to the analyzer system.

For the purposes of illustration only, the analyzer system 60, as illustrated in FIG. 2, is used as an example in the determination of total sulfur in a flare gas line 20. It is preferred that the gas sample 20, is sent from the sample valves SV1 30 and SV2 40, to an optional splitter valve 61. For this particular application, a portion of the sample gas 20, is introduced to a FID (Flame Ionization Detector) 63, where the sample 20, is burned in a hydrogen air flame. If hydrocarbons are present then the burning of the sample 20, in a hydrogen air flame will produce water and carbon dioxide. If sulfur containing compounds are present then they will be converted into sulfur dioxide. If carbon is present in the sample 20, then carbon dioxide will be produced during the burning of the sample 20, in the hydrogen air flame. The burning of the sample 20, in the hydrogen air flame creates an effluent sample 90. The effluent sample 90, from the FID 63, is then sent to a FPD SV (Sample Valve) 70. A portion of the effluent sample 90, may be injected into a chromatographic column set where the sulfur dioxide is separated from the water, carbon dioxide, and nitrogen. The sulfur dioxide is measured with a FPD (Flame Photometric Detector) 66.

FPD SV (Sample Valve) 70, is preferably a 10-port valve, comprising ports 71, 72, 73, 74, 75, 76, 77, 78, 79 and 80, and where sample loop 87, connects port 79 with port 72. In an inactive or relaxed state port 71 is connected to port 72, port 73 is connected to port 74, port 75 is connected to port 76, port 77 is connected to port 78, and port 79 is connected to port 80, for the flow path, as shown in FIG. 2, with solid lines. However, in an active state port 71 is connected to port 80, port 72 is connected to port 73, port 74 is connected to port 75, port, and port 78 is connected to port 79, for the flow path, as shown in FIG. 2, with dashed lines. It should be appreciated that port 76 and port 77 are never connected. However, for most applications, in an inactive mode or state the sample 90, is sent from port 71 to port 72, from port 72 to port 79 via sample loop 87, and then from port 79 to port 80, and is then sent to the vent 67, via FPD 66. Whereas, in an active mode or state the sample 90, is sent from port 71 to port 80, and is then sent to the vent 68.

For some applications, sample 20, from line 18, is sent to a split vent 62, via the splitter valve 61. However, for all applications the splitter valve 61, will send at least some of the sample 20, to the FID 63, via at least one restrictor 64. It should be appreciated that portion of the sample 10 and 20, is usually sent to the split vent 62, via the splitter valve 61, when the sample 10 and 20, are too large for processing by the FID 63.

A portion of effluent sample 90, may be sent to at least one chromatographic column 1 86 where water is separated from the rest of the components in the effluent sample 90. The rest of the components in the effluent sample 90, which consist of mainly air, carbon dioxide and sulfur dioxide, are then sent to column 2 88. After the air, carbon dioxide and sulfur dioxide have passed though column 1 86, to column 2 88, and the valve 70, is activated. With column 1 86, in the active state, water is back-flushed from column 1 86 through port 78, to port 77 and restrictor 82 to the back-flush vent 84. The sulfur dioxide continues to pass through column 2 88, where the sulfur dioxide is separated from the other components in the sample and passed to the FPD 66 for processing, and then to vent 67.

The FPD SV 70, and related components are preferably located in a temperature controlled environment 100, such as, an oven 100.

It should be appreciated that in this invention the carrier fluid 10, is known and the fluid flow of the carrier fluid 10, is kept constant, while the sample fluid 20, is unknown and changing, and the combination of the two fluids keep the sample flow constant while the unknown component of the sample fluid 20, is analyzed in the analyzer system 60, after being processed by either SV1 30 or SV2 40. Thus, even with the viscosity changes or composition changes of the fluid sample 20, the fluid flow rate within SV1 30 or SV2 40, remains the same or constant.

The analyzer system 60, can be calibrated by introducing a calibration mixture in the sample introduction system 23, using a calibration valve 26, from a calibration sample 24, as illustrated in FIGS. 1A and 1B.

The analyzer system 60, that is illustrated in FIG. 2, is illustrated having at least one detector and wherein the detector is selected from a group consisting of a Flame Ionization Detector (FID) 63, and a Flame Photometric Detector (FPD) 66. However, the analyzer system 60, could be selected from a group consisting of a UV Analyzer 60, a chemluminescence analyzer 60, an ultraviolet fluorescence analyzer 60, a themoconductivity analyzer 60, an X-ray fluorescence analyzer 60, and a photo ionization analyzer 60.

This invention allows for the analysis of a fluid sample 20, whose viscosity may be changing, such that, the viscosity of the sample fluid 20, processed at time t1, may be the same or may be different than the viscosity of a sample fluid 20, processed at time t2.

Similarly, this invention allows for the analysis of a fluid sample 20, whose material composition may be changing, such that, the material composition of the sample fluid 20, processed at time t1, may be the same or may be different than the material composition of a sample fluid 20, processed at time t2.

While the present invention has been particularly described in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

What is claimed is:

1. An apparatus for continuous, constant, flow sample introduction, comprising:
   (a) at least one sample line having at least one sample fluid;
   (b) at least one sampling system for processing said at least one sample fluid;
   (c) at least one electronic pressure controller for processing at least one carrier fluid; and
   (d) at least one first sampling valve and at least one second sampling valve, wherein said first sampling valve is connected to said second sampling valve in series, and wherein said first sampling valve and said second sampling valve are configured such that while said first sampling valve is processing said fluids to be analyzed the second sampling valve is being replenished with fluids to be analyzed to provide continuous flow sample introduction to an analyzer and wherein said fluids to be analyzed comprise said at least one sample fluid and said at least one carrier fluid.

2. The apparatus of claim 1, wherein said carrier fluid is selected from a group consisting of Argon, Helium and Nitrogen.

3. The apparatus of claim 1, wherein a known amount of at least one calibration sample fluid from a calibration sample unit is sent to said at least one first sampling valve or said at least one second sampling valve.

4. The apparatus of claim 1, wherein a known amount of at least one calibration sample fluid from a calibration sample unit is sent to said at least one first sampling valve or said at least one second sampling valve and wherein said calibration sample fluid from said calibration sample unit is selected from a group consisting of argon, helium, propane, methane, ethane and nitrogen.

5. The apparatus of claim 1, wherein said flow rate for said sample fluid flow is between about 150 mL/min to about 250 mL/min.

6. The apparatus of claim 1, wherein said flow rate for said carrier fluid flow is between about 0.50 mL/min to about 2.50 mL/min.

7. The apparatus of claim 1, wherein said apparatus has at least one analyzer system for receiving said fluid to be analyzed, and wherein said at least one analyzer system has at least one detector and wherein said detector is selected from a group consisting of a Flame Ionization Detector and Flame Photometric Detector.

8. The apparatus of claim 1, wherein said fluid to be analyzed is processed by at least one analyzer system, and wherein said analyzer system is selected from a group consisting of a UV Analyzer, a chemluminescence analyzer, an ultraviolet fluorescence analyzer, a themoconductivity analyzer, an X-ray fluorescence analyzer, and a photo ionization analyzer.

9. The apparatus of claim 1, wherein said sample fluid is a liquid.

10. The apparatus of claim 1, wherein viscosity of said sample fluid processed at time t1 is different than the viscosity of a sample fluid processed at time t2.

11. The apparatus of claim 1, wherein material composition of said sample fluid processed at time t1 is different than the material composition of a sample fluid processed at time t2.

12. The apparatus of claim 1, wherein said first sampling valve and said second sampling valve are contained inside a temperature controlled environment.

13. The apparatus of claim 1, wherein said first sampling valve and said second sampling valve are contained inside a temperature controlled environment, and wherein said temperature controlled environment is an oven.

14. The apparatus of claim 1, having at least one restrictor between said at least one electronic pressure controller and said at least one first sampling valve and said at least one second sampling valve.

15. The apparatus of claim 1, having at least one atmospheric management vent connected to said at least one first sampling valve and said at least one second sampling valve via at least one atmospheric reference valve to provide atmospheric equilibrium to said at least one first sampling valve or said at least one second sampling valve.

16. A process for continuous, constant, flow sample introduction, comprising:
  (a) forwarding at least one sample fluid from at least one sample line to at least one first sampling valve or at least one second sampling valve via at least one sampling system;
  (b) forwarding at least one carrier fluid to said at least one first sampling valve or at least one second sampling valve via at least one electronic pressure controller;
  (c) processing a fluid to be analyzed in said first sampling valve or said second sampling valve, wherein said fluid to be analyzed comprises said at least one carrier fluid and said at least one sample fluid; and
  (d) wherein said at least one first sampling valve and at least one second sampling valve are connected in series, and wherein said first sampling valve and said second sampling valve are configured such that while said first sampling valve is processing said fluids to be analyzed the second sampling valve is being replenished with fluids to be analyzed to provide continuous flow sample introduction to an analyzer.

17. The process of claim 16, wherein said carrier fluid is selected from a group consisting of Argon, Helium and Nitrogen.

18. The process of claim 16, wherein a known amount of at least one calibration sample fluid from a calibration sample unit is sent to said at least one first sampling valve or said at least one second sampling valve.

19. The process of claim 16, wherein a known amount of at least one calibration sample fluid from a calibration sample unit is sent to said at least one first sampling valve or said at least one second sampling valve and wherein said calibration sample fluid from said calibration sample unit is selected from a group consisting of argon, helium, propane, methane, ethane and nitrogen.

20. The process of claim 16, wherein said flow rate for said sample fluid flow is between about 150 mL/min to about 250 mL/min.

21. The process of claim 16, wherein said flow rate for said carrier fluid flow is between about 0.50 mL/min to about 2.50 mL/min.

22. The process of claim 16, wherein said fluid to be analyzed is sent to at least one analyzer system, and wherein said analyzer system has at least one detector and wherein said detector is selected from a group consisting of a Flame ionization Detector and Flame Photometric Detector.

23. The process of claim 16, wherein said fluid to be analyzed is sent to at least one analyzer system, and wherein said analyzer system is selected from a group consisting of a UV Analyzer, a chemluminescence analyzer, an ultraviolet fluorescence analyzer, a themoconductivity analyzer, an X-ray fluorescence analyzer, and a photo ionization analyzer.

24. The process of claim 16, wherein said sample fluid is a liquid.

25. The process of claim 16, wherein viscosity of said sample fluid processed at time t1 is different than the viscosity of a sample fluid processed at time t2.

26. The process of claim 16, wherein material composition of said sample fluid processed at time t1 is different than the material composition of a sample fluid processed at time t2.

27. The process of claim 16, wherein said first sampling valve and said second sampling valve are contained inside a temperature controlled environment.

28. The process of claim 16, wherein said first sampling valve and said second sampling valve are contained inside a temperature controlled environment, and wherein said temperature controlled environment is an oven.

29. The process of claim 16, wherein said at least one carrier fluid is processed through at least one restrictor, and wherein said at least one restrictor is placed between said at least one electronic pressure controller and said at least one first sampling valve and said at least one second sampling valve.

30. The process of claim 16, wherein at least one atmospheric management vent is connected to said at least one first sampling valve and said at least one second sampling valve via at least one atmospheric reference valve, and wherein said at least one atmospheric management vent is used to provide atmospheric equilibrium to said at least one first sampling valve or said at least one second sampling valve.

31. An apparatus for continuous, constant, flow sample introduction, comprising:
  (a) at least one sample line having at least one sample fluid;
  (b) at least one sampling system for processing said at least one sample fluid;
  (c) at least one electronic pressure controller for processing at least one carrier fluid;
  (d) at least one first sampling valve and at least one second sampling valve, wherein said first sampling valve is connected to said second sampling valve in series, and wherein said first sampling valve and said second sampling valve are configured such that while said first sampling valve is processing said fluids to be analyzed the second sampling valve is being replenished with fluids to be analyzed, and wherein said fluids to be analyzed comprise said at least one sample fluid and said at least one carrier fluid; and
  (e) at least one analyzer system, wherein said analyzer system comprises at least one detector for analyzing said fluids to be analyzed wherein a flow sample is continuously provided to said analyzer system.

* * * * *